US005744366A

United States Patent [19]

Kricka et al.

[11] Patent Number: 5,744,366
[45] Date of Patent: *Apr. 28, 1998

[54] MESOSCALE DEVICES AND METHODS FOR ANALYSIS OF MOTILE CELLS

[75] Inventors: Larry J. Kricka, Berwyn; Peter Wilding, Paoli, both of Pa.

[73] Assignee: Trustees of the University of Pennsylvania, Philadelphia, Pa.

[*] Notice: The term of this patent shall not extend beyond the expiration date of Pat. No. 5,296,375.

[21] Appl. No.: 338,380

[22] Filed: Nov. 14, 1994

Related U.S. Application Data

[63] Continuation-in-part of Ser. No. 184,577, Jan. 21, 1994, Pat. No. 5,427,946, which is a continuation of Ser. No. 877,661, May 1, 1992, Pat. No. 5,296,375.

[51] Int. Cl.⁶ ................................................. G01N 33/483
[52] U.S. Cl. .......................... 436/63; 422/58; 422/61; 422/101; 422/102; 435/2; 435/288.5; 435/288.7; 436/165; 436/180; 436/807; 436/809; 600/33
[58] Field of Search .................... 422/55, 58, 61, 422/99, 101, 102; 436/524, 164, 165, 180, 501, 807, 809, 527, 63; 435/2, 7.2, 7.21, 286.5, 287.1, 287.2, 287.3, 288.3, 288.5, 288.7, 292.1, 297.5, 305.1, 305.2–305.4, 307.1; 600/33

[56] References Cited

U.S. PATENT DOCUMENTS

| | | | |
|---|---|---|---|
| 3,799,742 | 3/1974 | Coleman | 422/61 |
| 4,155,831 | 5/1979 | Bhattacharya | 204/299 R |
| 4,790,640 | 12/1988 | Nason | 350/534 |
| 4,804,537 | 2/1989 | Bergman et al. | 424/105 |
| 4,892,830 | 1/1990 | Findley et al. | 435/286.6 |
| 4,906,439 | 3/1990 | Grenner | 422/56 |
| 4,911,782 | 3/1990 | Brown | 156/633 |
| 4,963,498 | 10/1990 | Hillman et al. | 436/69 |
| 4,999,283 | 3/1991 | Zavos et al. | 435/2 |
| 5,147,606 | 9/1992 | Charlton et al. | 422/56 |
| 5,296,375 | 3/1994 | Kricka et al. | 422/58 X |
| 5,304,487 | 4/1994 | Wilding et al. | 422/58 X |
| 5,427,946 | 6/1995 | Kricka et al. | 422/58 X |
| 5,486,335 | 1/1996 | Wilding et al. | 422/55 |

FOREIGN PATENT DOCUMENTS

| | | |
|---|---|---|
| 2131972 | 6/1984 | United Kingdom. |
| 2220003 | 12/1989 | United Kingdom. |
| 9009596 | 8/1990 | WIPO. |
| 9115750 | 10/1991 | WIPO. |

OTHER PUBLICATIONS

Kricka et al. "Liquid Transport in Micron & Submicron Channels", *SPIE*, 1167–12, pp. 159–168, 1989.

*Primary Examiner*—Jan Ludlow
*Attorney, Agent, or Firm*—Dann, Dorfman, Herrell and Skillman

[57] ABSTRACT

Devices and methods are provided to facilitate the rapid, accurate analysis of a sample having cells characterized by their motility. The devices feature a solid substrate microfabricated to define a flow system including one or more ports or chambers, connected by elongate channels of various shapes having a mescoscale cross-sectional dimension on the order of 0.1 μm to 1000 μm. In one embodiment, the devices are fitted with various flow-regulating features to facilitate unimpeded movement of the motile cells of interest along the flow channels. In another embodiment, devices are provided for conducting replicate motile cell assays, or for conducting a series of different assays using a single test sample. In another embodiment, preparative devices are provided for separating and collecting selected motile cell types of interest. In another embodiment, a device designed for performing an in vitro fertilization is provided in a portable incubator, which maintains the in vitro fertilization under optimum conditions. The devices of the invention may be used in a wide range of applications, and are particularly applicable for analyses and preparation of sperm, as well as in vitro fertilization. The devices and methods of the invention are also suitable for various analyses of a wide variety of motile cells, such as motile microorganisms and chemotactic cells, and can be used in clinical tests as well as laboratory and field tests.

13 Claims, 8 Drawing Sheets

MESOSCALE DEVICES AND METHODS FOR ANALYSIS OF MOTILE CELLS

REFERENCE TO RELATED APPLICATIONS

This application is a continuation-in-part of co-pending U.S. application Ser. No. 08/184,577 filed Jan. 21, 1994 and issued as U.S. Pat. No. 5,427,946 on Jun. 27, 1995, which is a continuation of U.S. application Ser. No. 07/877,661, filed May 1, 1992, issued as U.S. Pat. No. 5,296,375 on Mar. 22, 1994, the disclosure of which is incorporated herein by reference. This application is being filed contemporaneously with commonly-owned U.S. Ser. No. U.S. application Ser. No. 08/338,728, filed Nov. 14, 1994, now U.S. Pat. No. 5,587,128, which is a continuation-in-part of U.S. Ser. No. 07/877,662, filed May 1, 1992, issued as U.S. Pat. No. 5,498,392 on Mar. 12, 1996, the disclosures of which are incorporated herein by reference. This application is also being filed contemporaneously with commonly-owned U.S. Ser. No. U.S. application Ser. No. 08/338,368 filed Nov. 14, 1994, which is a continuation-in-part of U.S. Ser. Nos. 07/877,702 (filed May 1, 1992), abandoned, 08/196,021 (filed Feb. 14, 1994) and 08/250,100 (filed May 26, 1994) now U.S. Pat. No. 5,486,335. All of the above-listed disclosures are incorporated herein by reference.

BACKGROUND OF THE INVENTION

This invention relates generally to methods and apparatus for conducting analyses. More particularly, the invention relates to the design and construction of small, typically single-use, modules capable of rapidly analyzing microvolumes of a fluid sample, with particular emphasis on analysis of motile cells.

In recent decades the art has developed a very large number of protocols, test kits and cartridges for conducting analyses on biological samples for various diagnostic and monitoring purposes. Immunoassays, immunometric assays, agglutination assays, and analyses based on polymerase chain reaction, various ligand-receptor interactions, and differential migration of species in a complex sample all have been used to determine the presence or concentration of various biological compounds or contaminants, or the presence of particular cell types.

Recently, small, disposable devices have been developed for handling biological samples and for conducting certain clinical tests. Shoji et al. reported the use of a miniature blood gas analyzer fabricated on a silicon wafer. Shoji et al., *Sensors and Actuators*, 15:101–107 (1988). Sato et al. reported a cell fusion technique using micromechanical silicon devices. Sato et al., *Sensors and Actuators*, A21–A23:948–953 (1990). A microprocessor-controlled laser photometer has been manufactured for detecting blood clotting (Ciba Corning Diagnostics Corp. USA).

Micromachining technology originated in the microelectronics industry. Angell et al., *Scientific American*, 248:44–55 (1983). Micromachining technology has enabled the manufacture of microengineered devices having structural elements with minimal dimensions ranging from tens of microns (the dimensions of biological cells) to nanometers (the dimensions of some biological macromolecules). Most experiments involving structures of this size have related to micromechanics, i.e., mechanical motion and flow properties. The potential capability of such structures has not been exploited fully in the life sciences.

Brunette (*Exper. Cell Res.*, 167:203–217 (1986) and 164:11–26 (1986)) studied the behavior of fibroblasts and epithelial cells in grooves in silicon, titanium-coated polymers and the like. McCartney et al. (*Cancer Res.*, 41:3046–3051 (1981)) examined the behavior of tumor cells in grooved plastic substrates. LaCelle (*Blood Cells*, 12:179–189 (1986)) studied leukocyte and erythrocyte flow in microcapillaries to gain insight into microcirculation. Hung and Weissman reported on fluid dynamics in micromachined channels, but did not produce data associated with an analytic device. Hung et al., *Med. and Biol. Engineering*, 9:237–245 (1971); and Weissman et al., *Am. Inst. Chem. Eng. J.*, 17:25–30 (1971). Columbus et al. utilized a sandwich composed of two orthogonally orientated v-grooved embossed sheets in the control of capillary flow of biological fluids to discrete ion-selective electrodes in an experimental multi-channel test device. Columbus et al., *Clin. Chem.*, 33:1531–1537 (1987). Masuda et al. and Washizu et al. have reported the use of a fluid flow chamber for the manipulation of cells (e.g. cell fusion). Masuda et al., *Proceedings IEEE/IAS Meeting*, pp. 1549–1553 (1987); and Washizu et al., *Proceedings IEEE/IAS Meeting* pp. 1735–1740 (1988). The potential of using very small scale devices for the analyses of biological fluids, cells and microorganisms has heretofore remained largely unexplored. Current larger-scale analytical techniques utilized for the detection or analysis of microorganisms and cells are rarely automated, generally not portable, and can often be slow and cumbersome. As a result, a need exists for convenient and rapid systems for clinical, laboratory, and field assays.

There is particularly a growing need for standardized procedures for the analysis of semen, capable of providing reliable and rapid results, which may be used in the assessment of male infertility, and also for a range of other applications including in vitro fertilization (IVF), artificial insemination by donor semen (AID) and forensic medicine (The World Health Organization, *WHO Laboratory Manual for the Examination of Human Semen and Semen-Cervical Mucus Interaction*, Cambridge University Press, Cambridge, U.K., 1987). The evaluation of male infertility through the analysis of semen involves a range of tests including the assessment of sperm count, motility, morphology, sperm antibodies, sperm cervical mucus interaction and sperm biochemistry. Wang et al., *American Association for Clinical Chemistry, Endo.* 10:9–15 (1992). There is a need for systems capable of conducting a range of rapid and reliable analyses of a sperm sample.

In U.S. Pat. No. 5,296,375, which is commonly owned with the present application, there are described various devices for analysis and manipulation of motile cells, such as sperm. These devices comprise a solid substrate microfabricated to define a sample inlet port and a mesoscale channel and chamber system.

Some of the features and benefits of devices constructed in accordance with the teachings disclosed U.S. Pat. No. 5,296,375 are summarized in Table 1. Those devices can be used to implement a range of rapid clinical tests for the analysis of a biological sample. With respect to sperm analysis, the devices can be used to implement a range of rapid clinical tests for the analysis of a sperm sample. The devices may be utilized, e.g., for the detection of the motility or morphology of a sperm sample or to test the presence of sperm antibodies, or to test the interaction of sperm with cervical mucus, or other assays used in infertility testing. In addition, the devices may be utilized to test the interaction of a sperm sample with other reagents such as spermicides. The invention described in U.S. Pat. No. 5,296,375 provides methods and devices for use in a wide range of possible assays. Assays may be completed rapidly, and at the conclusion of the assay the chip can be discarded, which advantageously prevents contamination between samples, entombs potentially biologically hazardous material, and provides an inexpensive, microsample analysis.

TABLE 1

| Feature | Benefit |
| --- | --- |
| Flexibility | No limits to the number of device designs or applications available. |
| Reproducible | Allows reliable, standardized, production of devices. |
| Low Cost Production | Allows competitive pricing with existing systems. Disposable nature for single-use processes. |
| Small Size | No bulky instrumentation required. Lends itself to portable units and systems designed for use in non-conventional lab environments. Minimal storage and shipping costs. |
| Microscale | Minimal sample and reagent volumes required. Reduces reagent costs, especially for more expensive, specialized test procedures. Allows simplified instrumentation schemes. |
| Sterility | Devices can be sterilized for use in microbiological assays and other procedures requiring clean environments. |
| Sealed System | Minimizes biohazards. Ensures process integrity. |
| Multiple Circuit Capabilities | Can perform multiple processes or analyses on a single device. Allows panel assays. |
| Multiple Detector Capabilities | Expands capabilities for assay and process monitoring to virtually any system. Allows broad range of applications. |
| Reusable Devices | Reduces per process cost to the user for certain applications. |

Ongoing research involving the above-mentioned devices has led to the discovery of a number of modifications and additions to the devices that can improve their effectiveness for analyses of sperm and other motile cells. Devices and methods incorporating these improvements are set forth in detail in the description, drawings, and claims which follow.

SUMMARY OF THE INVENTION

The invention provides methods and apparatus for analyzing cell motility and for measuring other properties of cells of interest. The devices of the invention may be used in a range of applications, including sperm motility and morphology testing and in vitro fertilization, as well as motility and morphology testing of other cell types including various microorganisms and chemotactic cells.

According to one aspect of the invention, a device is provided for analyzing a sample having cells characterized by their motility. The device comprises a solid substrate having a flow system which includes at least one elongate flow channel of mesoscale cross-sectional dimension, and a receiving well communicating with the channel and defining a starting point in the channel. The device further comprises a cover for the substrate, which closes the channel and has a port in registry with the receiving well, for introducing the sample into the receiving well. Motile cells in the sample travel from the receiving well to various progress points along the channel. The cover of the device also defines a second port to the channel at some point along the channel, preferably distal to the receiving well. In one embodiment, the second port comprises a hole in the cover in registry with the channel at point therealong. In another embodiment, the channel extends to an edge of the substrate and the port is formed at that edge upon closing the channel with the cover.

In another embodiment, the above-described device further comprises a target chamber communicating with the channel and defining a terminating point in the channel. In this embodiment, the second port is preferably in registry with the target chamber.

The devices of the present invention comprise a number of features for regulating the flow of a sample fluid from the receiving well into the mesoscale flow channel. According to one aspect of the present invention, the device described above is provided with a seal for the second port, for sealing the second port during introduction of the sample into the receiving well. The seal may be permanent or removable. In accordance with the present invention, it has been discovered that this modification significantly reduces sudden bulk ingress of the sample fluid from the receiving well to the channel, thereby ensuring that cell movements observed in the flow channel are due to the inherent motility of the cells being assessed, and not to the flow properties of the sample fluid.

According to another aspect of the invention, devices are provided wherein the receiving well further includes a plurality of flow-regulating solids having a size and shape effective to permit passage of non-aggregated motile cells of interest from the receiving well into the channel and concomitantly to substantially restrain passage into the channel of other particulate matter in the sample, such as cellular aggregates, large particles, gelatinous material and the like. In one embodiment, the flow-regulating solids, such as glass or latex beads, are added to the receiving well. In another embodiment, the flow-regulating solids comprise an array of projections fabricated in the substrate at a position in the receiving well adjacent to the communicating terminus of the channel.

According to another aspect of the present invention, a device is provided wherein the receiving well further includes a cell director comprising flow-guiding ribs longitudinally aligned with the channel for directing motile cells in the sample from the receiving well into the channel.

The devices of the present invention also comprise several modifications facilitating their utility as preparative devices, i.e. for separation and/or collection of motile cells of interest. According to one aspect of the present invention, devices such as those described above are provided wherein the cover includes at least one additional port in registry with at least one progress point along the channel, thereby providing access to motile cells disposed in the channel at that progress point. In one embodiment, the flow system of this device further comprises at least one sampling chamber disposed along the channel at the progress point, in fluid communication with the channel. In this embodiment, the cover comprises at least one additional port in registry with the sampling chamber.

According to another aspect of the invention, a preparative device is provided in which the channel comprises a tortuous region and selection region, the selection region being adapted for selective separation of a least one motile cell type from a mixed population of cell types. In one embodiment, the selection region comprises a capture agent which selectively binds the cell type of interest, or alternatively to another cell type in the mixed population, with fluid flow in the channel thereafter separating the captured cell type from the unrestrained cell type. Optionally, two or more target chambers may be provided for collecting two or more motile cell types of interest. In another embodiment, the selection region comprises an electric field which selectively influences motility of the cell type of interest, thereby effecting separation of that cell type from other cells in the mixed population.

According to yet another aspect of the present invention, an apparatus is provided for performing an in vitro fertilization. The apparatus includes a device of the invention, which comprises a solid substrate and at least one elongate flow channel of mesoscale cross-sectional dimension, a receiving well communicating with the channel and defining a starting point in the channel, an egg nesting well communicating with the channel and defining a terminating point in the channel, and a cover for the substrate which closes the channel and has a port for introducing a sperm sample in the receiving well, and another port in registry with the egg nesting well. The device is disposed in a portable, sealable, environmental control chamber, which includes a holding region for holding the device, and optionally a temperature regulating system and/or a humidity control system. The apparatus may also include a system for producing an atmosphere in the chamber conducive for the in vitro fertilization.

Various methods are provided for operating the devices of the invention described above. According to one aspect of the invention, a method is provided for analyzing a fluid sample having cells characterized by their motility. A device is provided which comprises a solid substrate having a flow system comprising at least one elongate channel of mesoscale cross-sectional dimension and a receiving well communicating with the channel and defining a starting point in the channel. The device includes a cover for the substrate which closes the channel and possesses a port in registry with the receiving well; the cover further defines a second port in registry with the channel at a point therealong. The flow system of the device is filled with a carrier fluid, and the test sample is introduced into the receiving well. The resident conditions of the combined carrier fluid and the test sample are controlled to assure motility of the cells in the carrier fluid. The cells are observed in the test sample as they travel from the receiving well to various progress points along the channel, which may be observably marked, and data are collected based on those observations. The analysis is completed using the data collected.

In one embodiment, the resident conditions of the combined carrier fluid and test sample are controlled by sealing the second port of the device prior to introducing the test sample into the receiving well. The seal may be permanent or it may be removed after the assay is complete. In another embodiment, the resident conditions are controlled by providing in the receiving well a plurality of flow-regulating solids, having a size and shape effective to permit passage of the motile cells from the receiving well into the channel and concomitantly to substantially restrain passage into the channel of selected particulate matter in the test sample. In another embodiment, the resident conditions are controlled by providing in the receiving well a cell director comprising flow-guiding ribs longitudinally aligned with the channel, which function to direct the motile cells from the receiving well into the channel.

According to another aspect of the present invention, a method is provided similar to that described above, which further includes generating replicate sets of data by conducting the above-described method in a device which further comprises a plurality identical flow systems. By conducting the methods simultaneously in each of the plurality of flow systems, replicate sets of data for the analysis are generated.

According to another aspect of the present invention, the methods described above further include conducting a plurality of different analyses on a single sample. For this method, a device of the invention is provided which further comprises a multiplicity of non-identical flow systems designed for the plurality of analyses, each flow system being filled with a carrier fluid which optionally contains reagents for each analysis. An aliquot of the sample is introduced into each receiving well, and the cells in each flow system are observed. Data are collected based on those observations, and the analyses are made using the data.

According to yet another aspect of the present invention, a method is provided as described above which further includes selectively separating and optionally collecting a least one motile cell type from a sample comprising a mixed population of cell types. In this method, a device is provided in which the flow channel comprises a selection region, adapted for selected separation of a cell type of interest and, optionally, for two or more cell types of interest. The sample is introduced into the receiving well, whereafter the mixed population of cell types migrates through the selection region of the channel, resulting in selective separation of the motile cell type of interest from the mixed population of cell types. The motile cell type can then be collected.

According to still another aspect of the present invention, a method is provided for performing in vitro fertilization. An in vitro fertilization device, as described above, is filled with appropriate in vitro fertilization medium, one or more eggs in the egg nesting well and a sperm sample in the receiving well. The in vitro fertilization device is then placed in a portable, sealable, environmental control chamber for a time and under conditions effective to enable the sperm to reach and fertilize the egg.

The devices and methods of the invention may be used in a wide range of assays to rapidly generate an accurate assessment of cell motility, as well as other features of motile cells of interest, from a single test sample. The numerous features and benefits of the device and methods of the present invention will become apparent from the following description, examples and drawings.

BRIEF DESCRIPTION OF THE DRAWINGS

Like reference characters in the respective drawn figures indicate corresponding parts. The drawn figures are not necessarily to scale.

DETAILED DESCRIPTION

Figure 1:
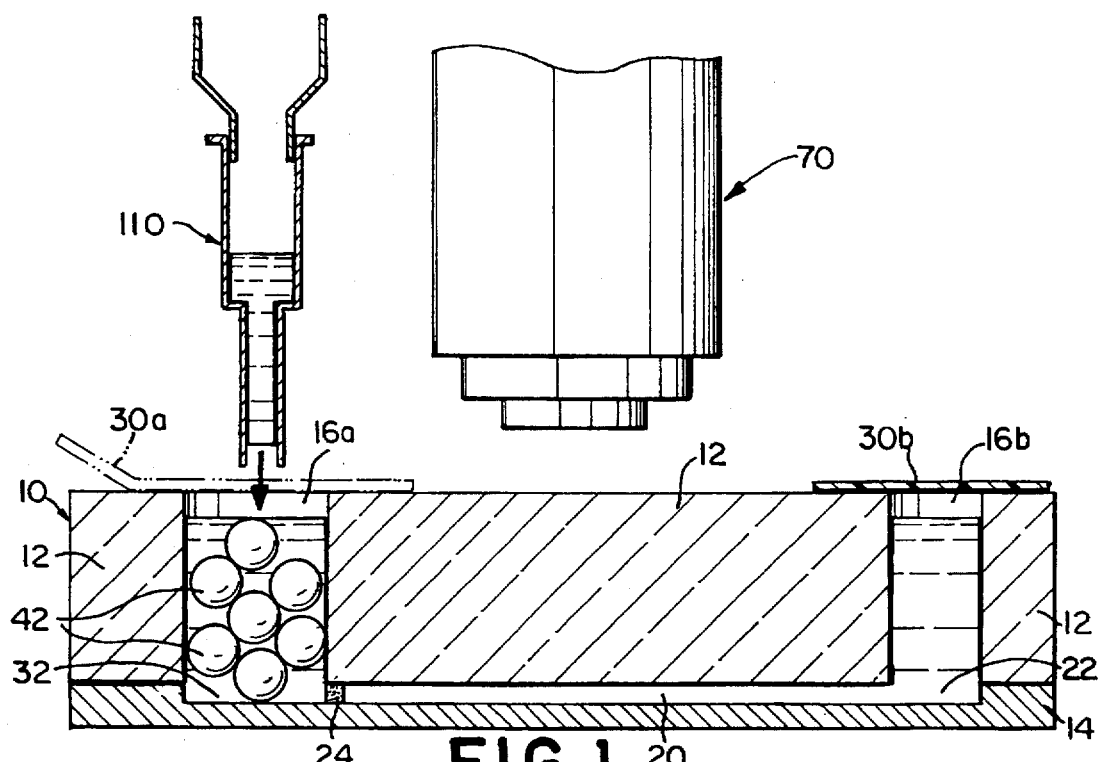
FIG. 1 is a diagrammatic view of device 10 according to the invention having a substrate 14 and cover 12 with a receiving well 32 for accepting a test sample introduced by a delivery apparatus 110, such as a pipette or syringe, via an inlet port 16a, the device having a mesoscale flow channel in which the sample may be viewed by a an optical system 70, such as a microscope. Ports 16a and 16b over receiving well 32 and target chamber 22, respectively, are sealed by seals 30a and 30b respectively, the removable seal 30a for the receiving well being shown in broken lines. Receiving well 32 and inlet port 16a are shown filled with flow-regulating particles 42, and a mesoscale filter 24 is disposed at the entrance of flow channel 20.

The present invention provides devices and methods for analysis of cell motility, which may be utilized in a wide range of clinical, laboratory and field applications. The devices and methods of the invention are particularly applicable for sperm handling, including sperm motility and morphology testing, sperm count, analysis of sperm viability, sperm penetration assays (e.g., through cervical mucus or hyaluronic acid), analysis of surface antigens, preparative separation of sperm, and in vitro fertilization. The devices and methods of the invention are also suitable for various analyses of a wide variety of motile cells, including, but not limited to, motile forms of bacteria, cyanobacteria and fungi, (e.g., slime molds), motile gametes such as sperm and zoospores, motile, unicellular plants and animals (e.g., protozoa, amoebae, Euglena) and chemotactic cells (i.e., cells that can be induced to motility by exposure to various chemical compounds). The devices and methods may be utilized in clinical tests (e.g., manipulation of sperm and in vitro fertilization, as described above), as well as in laboratory tests (e.g., screening of various cellular chemoattractants and chemorepellents) and in fields tests in the environmental and biological sciences (e.g., motility assessment of microorganisms in an ecosystem, under various environmental conditions). Thus, although sperm handling and in vitro fertilization are often described and exemplified herein, those skilled in the art will appreciate that the devices and methods of the invention may be utilized in wide variety of motile cell assays, as described above.

The devices of the invention (sometimes referred herein as "chips") comprise a solid substrate, fabricated to include a receiving well and a mesoscale flow channel system extending from the receiving well. Depending on the type of assay for which the chip is designed, the flow channels may terminate in a target chamber. However, for many embodiments, this is not required. The flow channels may simply terminate within the substrate, or alternatively may extend to an edge of the substrate.

In one embodiment, a sperm sample is introduced to the receiving well via an inlet port and the extent of migration of the sperm through a flow system, which usually comprises a tortuous flow channel extending from the receiving well, can serve as an indication of, e.g., the motility or morphology of the sperm sample. In another embodiment, a target chamber may be included in the device to serve as an egg nesting chamber, connected to the receiving well via an elongate channel of mesoscale cross-sectional dimension. A sperm sample is applied to the receiving well, and sperm in the sample then migrate competitively through the channel to the egg nesting chamber, where fertilization of the egg occurs.

At least one of the chambers and/or flow channels of the device has a mesoscale dimension, i.e., at least one cross-sectional dimension on the order of 0.1 to 1000 µm, more commonly less than 500 µm. Flow channels leading to chambers have preferred widths and depths on the order of about 2.0 µm to 300 µm, more preferably 3.0 µm to 100 µm. For many applications, channels of 5–50 µm widths are useful. Chambers in the substrate may have one or more larger dimensions, e.g., widths and/or lengths of a few millimeters. Preferred depths of channels and chambers are on the order of 0.1 to 100 µm, typically 2–50 µm. In embodiments for analysis of human sperm, channels are typically about 100–150 µm wide and about 40 µm deep. The width is selected so as not to constrain tail movement of the sperm. Since sperm size and tail length varies among species, widths should be selected depending on the species from which the sperm sample is taken. The depth of the chambers in the device optionally may be of mesoscale dimension (i.e. less than 1,000 µm, but the chambers generally have larger widths and lengths, e.g., on the order of 1 mm or larger. Typically, the entire device is of a length and/or width ranging from approximately 0.1 to a few (e.g., 5) centimeters. Devices of the invention also may include multiple ports and channels, in fluid communication with one or more chambers. The port(s), channel(s) and/or chamber(s) may be fabricated in the substrate or, alternatively, in a cover disposed over the substrate, or both.

Devices comprising a solid substrate and optionally a cover disposed over the substrate, can be designed and fabricated with mesoscale flow channels and/or chambers from a wide range of materials. The devices optionally may be fabricated from a material which can be sterilized easily. Silicon provides a useful material because of the well-developed technology permitting its precise and efficient fabrication. However, a wide range of other material may be used within the scope of the invention. Alternative preferred materials for fabricating substrates of the invention include translucent or transparent materials such as quartz, glass, diamond, polycarbonate, polystyrene, or other organic polymers such as polytetrafluoroethylenes. These materials are preferred in embodiments wherein a transparent device is desirable, e.g., for use with viewing devices wherein viewing is accomplished by passing electromagnetic energy through a sample. Other materials that may be utilized include, e.g., gallium, arsenide, indium phosphide, aluminum, polysilicon, silicon nitride, silicon dioxide, polyamide, various superalloys, zircaloy, steel, gold, silver, copper, tongueston, molybdenum, tantalum, KOVAR™, ceramic, KEVLAR™(aramid resin), KAPTON™ (polyimide film), MYLAR™(polyester film), brass, sapphire, or any of a range of plastics and organic polymeric materials available in the art.

The various ports, channels and chambers, as well as other functional elements of the device may be fabricated inexpensively in large qualities from, e.g., a silicon substrate by any of a variety of micromachining methods known to those skilled in the art. Micromachining methods available include film deposition processes such as chemical vapor deposition, laser-based fabrication or photolithographic techniques such as UV or X-ray processes, LIGA processes or plastic molding, or etching methods which may be performed by either chemical processes or plasma processes (see, e.g. Manz, et al., *Trends in Analytical Chemistry* 10: 144–149, 1991). The arrangement of channels, chambers, and ports facilitate the sequential, properly timed and volumetrically correct addition of samples and reagents within the devices.

Flow channels of varying widths and depths can be fabricated with mesoscale dimensions for use in analyzing sperm samples. The substrate containing a fabricated mesoscale flow channel may be covered and sealed, e.g., clamped or anodically bonded, with a thin glass cover. Other clear or opaque cover materials may be used, including various organic polymers such as polycarbonate, polystyrene, polyethylene, and the like. Alternatively, two substrates can be sandwiched, or a substrate can be sandwiched between two transparent covers. This embodiment is particularly useful if the various channels and chambers in the substrate are fabricated to span the entire depth of the substrate. The covers then form a transparent top and bottom surface of the device, which is convenient for viewing the sample with a conventional microscope. Thus, transparent covers can be used to form windows that facilitate dynamic viewing of the channel contents, and allow optical probing of the mesoscale flow system either visually or by machine. Other fabrication approaches may be used.

The capacity of the devices of the invention is small, enabling assays to be performed on very small amounts of a liquid sample (e.g., less than 50 µl and preferably less than 10 µl). The mesoscale devices may be fabricated for use with microliter volumes, or alternatively nanoliter volumes or less, which advantageously limits the amount of sample, buffer or other fluids required for an analysis. The devices may be used to implement a variety of automated, sensitive and rapid analyses, including various sperm characterization assays. At the conclusion of an assay, the devices may be cleaned and re-used, or discarded. The use of disposable devices eliminates contamination and reduces biohazard.

The devices of the invention containing a mesoscale channel system can be used in combination with an appliance for delivering and receiving fluids to and from the devices, which may incorporate a nesting site for holding the device, and for connecting ports on the device, with a flow line in the appliance. The appliance may also include a pump, which may be used to inject or withdraw sample fluids into or from the device. Alternatively, the sample may be injected into the device, by e.g., syringe or pipette or may enter the flow system simply by capillary action. Devices such as valves and other mechanical sensors for detecting sample fluid in the devices can be fabricated directly on the substrate and can be mass-produced according to well established technologies. Angell et al., *Scientific American*, 248:44–55 (1983). Alternatively, sensors such as optical detectors and other detection means may be provided in the appliance utilized in combination with the device. In another embodiment, the substrate may be disposed, e.g., in an appliance, at an angle with respect to a horizontal plane, to provide an incline for the travel of a sperm sample, to further enhance the detection of motility.

The devices of the invention also may be utilized in combination with an appliance for viewing the contents of the devices. The viewing appliance may comprise a microscope for viewing the contents of the chambers and channels in the devices. The appliance may also include a camera, an optical system, and a tilt mechanism for holding the device, and allowing the placement and angle of the device to be adjusted manually.

The devices may be microfabricated with a mesoscale flow channel that includes a detection region for detecting a component of a sperm sample, such as sperm antibodies or hormones. The detection region may comprise a binding moiety, capable of binding to a predetermined component of the cell sample. The binding moiety, such as an antigen binding protein, may be immobilized on the surface of the flow channels, or on a solid phase reactant such as a bead. The detection chamber may be utilized in a range of binding assays, e.g., to assay the interaction of a sperm sample with cervical mucus, to test the efficacy of spermicides, to assay for the presence of antibodies or contaminants in the sample, or to conduct sperm counts. The devices also may be fabricated with various thermal regulating systems for controlling temperature in one or more of the wells, channels and chambers.

The foregoing features of devices of the invention are described in greater detail in commonly owned U.S. Pat. No. 5,296,375, incorporated herein by reference. The use of a binding moiety for assays in a mesoscale detection chamber, as well as techniques for providing the binding moiety in the detection chamber, are disclosed in commonly-owned co-pending Application Ser. No. 07/877,702, filed May, 1, 1992 abandoned, the disclosure of which has been incorporated herein by reference. Thermal regulation in devices of the invention is described in greater detail in commonly-owned co-pending Application Ser. No. 08/308,199, filed Sep. 19, 1994, issued as U.S. Pat. No. 5,498,392 on Mar. 12, 1996, the disclosure of which has been incorporated herein by reference.

The devices of the invention may be used to perform a variety of cell motility assays and related manipulations. A typical device of the present invention is illustrated schematically in FIG. 1. Device 10 includes a substrate 14 and a cover 12, fabricated with ports 16a and 16b, receiving well 32 and target chamber 22, connected by mesoscale flow channel 20. A mesoscale filter 24, such as those described in commonly-owned U.S. Pat. No. 5,296,375, is optionally placed at the mouth of flow channel 20. The cover 12 is fabricated with ports 16a and 16b to fit directly over and register with the receiving well 32 and target chamber 22 respectively. Placement of cover 12 together with substrate 14 results in the formation of an enclosing wall of flow channel 20, leaving receiving well 32 and target chamber 22 open to the atmosphere via ports 16a and 16b. In an alternative embodiment, the target chamber may be omitted, but should be replaced with a port, disposed anywhere over the flow system, to facilitate filling or evacuating the device.

In practice, after hydraulically filling all channels with an appropriate biological medium (e.g., a buffer or a specific cellular medium, such as cervical mucus as a liquid sperm medium) a sample comprising the motile cell of interest (e.g. a sperm sample) is applied at inlet port 16a, optionally by way of a delivery apparatus 110, such as a pipette or syringe. Motile cells in the sample migrate from receiving well 32 into flow channel 20 toward target chamber 22. The extent of progress of motile cells along the flow channel 20 may serve as an indicator of cellular motility. The migration of motile cells may be detected optically, e.g. either visually or by means of an optical device 70, such as a microscope, through a transparent cover 12 over the flow channel 20 and/or target chamber 22 or through a transparent region of the substrate itself.

To maximize the utility of the devices of the invention, it is important to ensure that any cell movement observed in the flow channel is due to the inherent motility of the cell being assessed. Hence, fluid flow properties in the devices should neither impede nor enhance the movement of cells in the flow channel. Additionally, the flow channels should contain no extraneous material (i.e. particulate or agglomerate material other than the cells of interest) that could impede motility of the cells of interest or obscure visibility of the cells in the flow channels. The devices of the present invention include several modifications and additions to the devices disclosed in U.S. Pat. No. 5,296,375, which function to control fluid flow properties in the device flow channel and to exclude extraneous cellular aggregates, gelatinous bodies, non-cellular particulate material and the like from the flow channels of the device.

It has been discovered in accordance with the present invention that sudden bulk ingress of the sample from the receiving well into the flow channel may be minimized by sealing one or more distal access ports, preferably the access port to the target chamber, with sealing tape or another type of sealant. This feature is illustrated in FIG. 1, wherein port 16b disposed above and in registry with target chamber 22 is sealed with sealant 30b. This sealing improves the flow properties of the sample through flow channel 20 by minimizing bulk ingress of the sample into the channel, thereby reducing hydraulic shock and the effect thereof on motile cells contained within the sample. As a result, the movement characteristics of the motile cells in the sample can be measured and observed more accurately, without the confounding effects of bulk fluid flow through the flow channel.

In practice, the distal port is initially open to the atmosphere (or attached to an appropriate pressure/suction device) to facilitate filling the channels and chambers with a suitable biological medium. The distal port is then sealed, and a sample containing the motile cells of interest is introduced into the receiving well. After the assay is complete, the seal may be removed. Alternatively, a permanent seal (e.g. a hardening resin or glue) may be used, e.g., in disposable devices designed for single usage.

In addition to sealing the target chamber access port and/or other access ports of the device, the access port disposed over the receiving well may be also be fitted with a removable seal. Sealing the receiving well may be performed to preserve sterility of the device and/or to contain pre-packaged solutions and reactants in the device. As illustrated in FIG. 1 inlet port 16a is covered with a removable seal 30a.

It has also been discovered in accordance with the present invention that the flow properties of a motile cell-containing sample in the flow channels of the devices may be further regulated by including in the receiving well a plurality of flow-regulating solids, such as small beads or other particles, sometimes referred to herein as "flow-regulating particles." Flow regulating particles may be comprised of glass, latex beads, or similar particulate material, preferably having a rounded shape and smooth surface, so as to avoid damaging motile cells of interest in the receiving well. Other materials suitable for use in flow-regulating beads include but are not limited to: silica, plastics, organic polymers, metals and metal oxides. The flow-regulating particles improve the flow properties of sample fluid in the flow channels in two ways. First, they function to fractionate the flow pattern of the sample fluid added to the receiving well, thereby further reducing ingress of bulk sample into the channel. Second, the particles function to restrict entry into the flow channel of cellular aggregates, large particles, gelatinous material and the like, so that only the motile cells of interest enter the flow channel. This enables the motile cells of interest to proceed along the flow channel unimpeded by extraneous material originally present in the sample, and also facilitates visual observation of the cells by eliminating material from visual inspection regions that could obscure viewing of the motile cells.

A device that includes flow-regulating particles is illustrated schematically in FIG. 1. As can be seen in FIG. 1, inlet port 16a and receiving well 32 together contain flow-regulating particles 42. It will be appreciated that flow-regulating particles 42 should be of a size and shape to enable passage between the particles of the motile cells of interest, but entraining, and thereby restricting from the flow channel, larger cell aggregates, gelatinous material, non-cellular particulate matter, and similar materials that may be present in the sample. Thus, the size and shape of the flow-regulating particles should be selected with reference to the motile cell types to be tested in the devices of the invention. Accordingly, glass or latex beads, which may be fabricated to varying sizes, are particularly suitable for use as flow-regulating particles.

Figure 3:
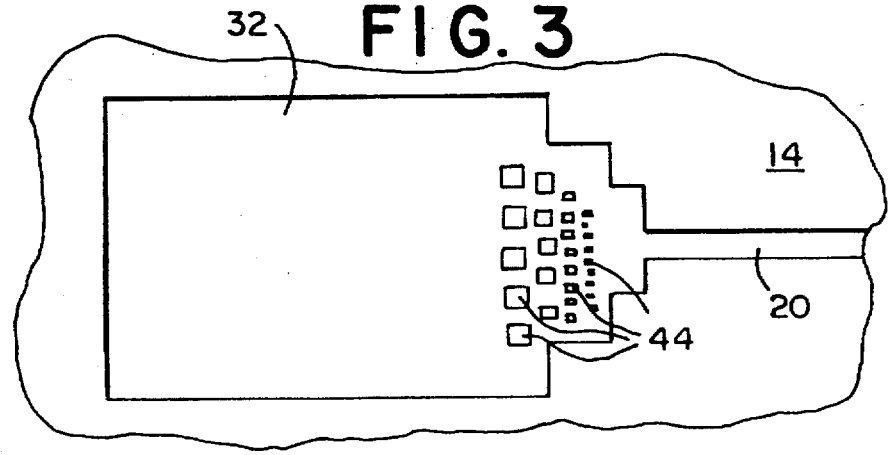
FIG. 3 is a face view of a substrate 14 of the type shown in FIG. 1, in which the bottom surface of receiving well 32 comprises a flow-regulating structure having a series of protruding posts 44 disposed adjacent to the entry of flow channel 20.

In another embodiment, flow from the receiving well in the flow channel is regulated by flow-regulating structure instead of, or optionally in addition to, flow-regulating particles. FIG. 3 schematically illustrates a face view of receiving well 32, microfabricated to comprise a series of flow-regulating structures 44, fabricated in the receiving well adjacent to flow channel 20. These flow-regulating structures 44 function in a manner equivalent to the flow-regulating particles described above, in that they fractionate the flow of the sample fluid, thereby reducing bulk ingress of sample fluid into the channel, and the also entrain large cellular aggregates, gelatinous material, etc, thereby excluding it from the flow channel. The flow-regulating structure 44 is of a size that enables passage of the motile cells of interest into the flow channel, but impedes larger particulate matter.

In another embodiment, devices of the invention may also be fabricated with mesoscale filters, such as those described in commonly owned U.S. Pat. No. 5,296,375, at the mouth of a flow channel. The mesoscale filter may either replace or supplement flow-regulating beads or structures. A device having a flow channel in which is disposed mesoscale filter 24 is diagrammatically illustrated in FIG. 1 and FIG. 2A.

Figure 2A:
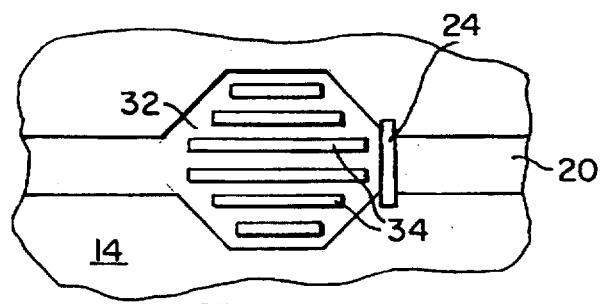
FIG. 2A is a fragmentary face view of a substrate 14 of the type shown in FIG. 1, in which the bottom surface of the receiving well 32 comprises a cell director having a parallel series of flow-guiding ribs 34 connected with flow channel 20.
Figure 2B:
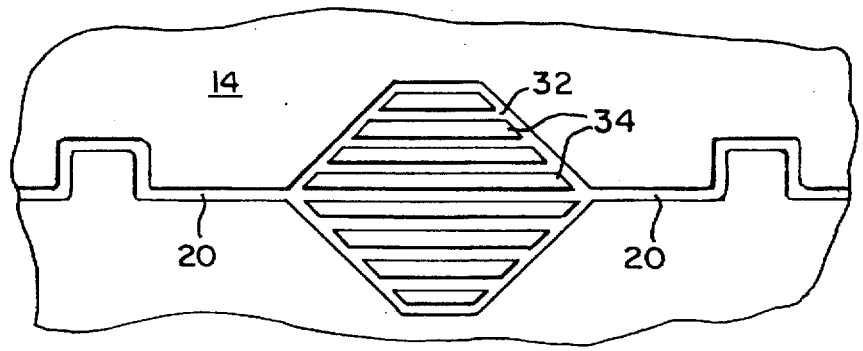
FIG. 2B is view similar to FIG. 2A, showing an alternative form of substrate 14 in which receiving well 32 is provided with flow-guiding ribs 34 and is connected with two similar mesoscale flow channels 20.

To ensure a high density of motile cells entering the flow channels, the base of the receiving well may be fabricated with a series of parallel flow-guiding ribs sometimes referred to herein collectively as "cell directors." The flow-guiding ribs orient motile cells and guide their entry into the flow channel. Without such a device fashioned into the receiving well, it has been found that sperm and other motile cells tend to swim into the corners of the receiving well, rather than entering the flow channel. One embodiment of a device having a receiving well with cell directors is shown in FIG. 2B. Substrate 14 in FIG. 2B shows receiving well 32 fabricated with flow-guiding ribs 34 directing motile cells into flow channel 20. Another embodiment of a device utilizing cell directors is shown in FIG. 2A. FIG. 2A shows substrate 14 fabricated with receiving well 32 having a series of parallel flow-guiding ribs 34, which direct motile cells into two flow channels 20 at opposing ends of receiving well 32.

In another embodiment, a prepartive device may be fabricated for separating and collecting motile cells on the basis of their comparative mobilities. A preparative motile cell collecting chip is particularly useful for collecting sperm of various mobilities. Such a device is shown schematically in FIG. 4. Device 10 comprises a substrate 14 having a receiving well 32 and a target chamber 22, connected by a tortuous flow channel 20. It is again noted that target chamber 22 may be omitted from the device. Depending on the type of motile cell being prepared, the flow channel may comprise square corners (i.e. corners at right angles), or alternatively, the corners may be somewhat rounded, such that the flow channel is serpentine in nature. Device 10 further comprises a cover 12, which is clamped or otherwise bonded to substrate 14. Cover 12 is fabricated with access ports 16, which register with the flow channel 20 at selected positions. Additionally, access ports 16 are aligned over and register with receiving well 32 and target chamber 22. One or more of the access ports 16 may be sealed with, e.g., sealing tape or a resin (not shown) before or during use of the device. In practice, a sample containing motile cells, such as sperm, is introduced into the receiving well. Thereafter, motile cells enter the flow channel, migrating along the flow channel to the target chamber. During a pre-determined time period, cells having greater motility will migrate further along the flow channel, such that motile cells become dispersed along the flow channel at various distances from the target chamber, depending on their relative mobilities. Samples containing motile cells at various positions along flow channel 20 may be removed via any of the access ports 16b, for analysis or further use.

Figure 5:
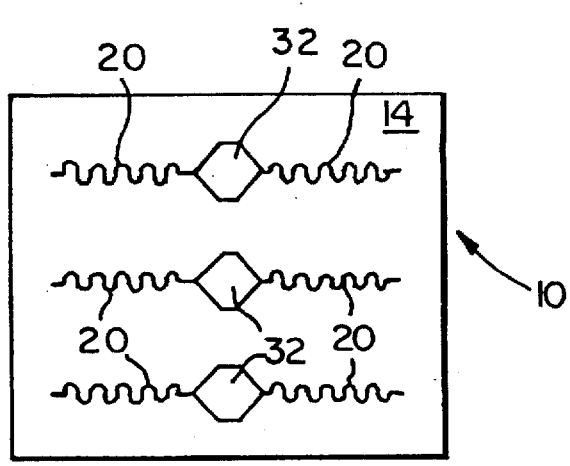
FIGS. 5, 6, and 7 are face views at a reduced scale, showing substrates 14 having multiple receiving wells 32, each connected to multiple flow channels 20, some of which terminate in separate or joined target chambers 22.
Figure 6:
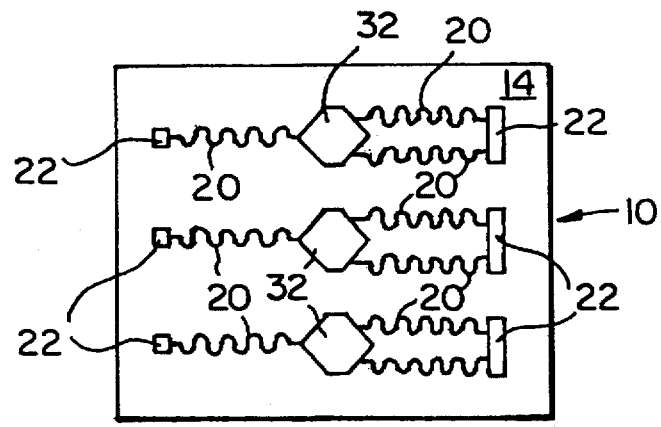
Figure 7:
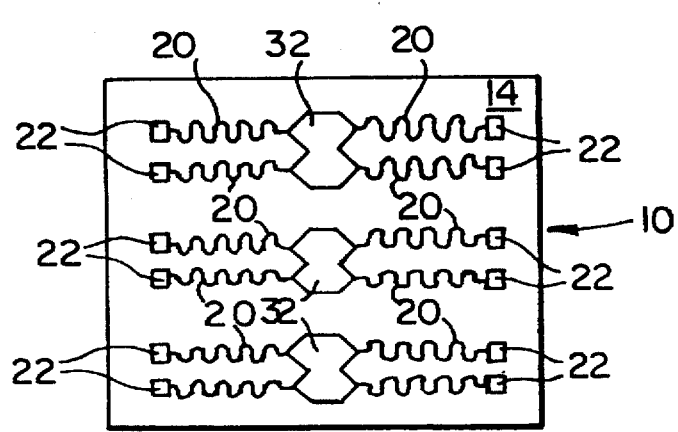

In another embodiment of the present invention, multiplicate cell motility assay chips are provided to improve the accuracy of cell motility assessment and to expand the scope of utility of the devices of the invention to a wider variety of assays. As illustrated in FIGS. 5–7, a substrate 14 is fashioned with a multiplicity of flow channels 20 (2,3,4, or more) extending from a single receiving well 32 and optionally terminating in target chambers 22. In the embodiment shown in FIG. 5, the flow channels 20 do not terminate in target chambers. In the embodiment shown in FIG. 6, one or more flow channels 20 may terminate in a common target chamber 22. In FIGS. 5 and 6, the receiving wells 32 are configured in a generally quadrilateral or rhombic form, whereas in FIG. 7, the wells 32 have a generally hourglass shape, whose diverging portions direct the sample into the multiple flow channels 20. One or more of the receiving wells may include a "cell director" comprising flow-guiding ribs. In practice, a single sample is applied to receiving well 32, and the motile cells thereafter migrate through identical channels 20, enabling multiple replication of a single assay and generation of an experimental result reflecting the mean value of the replicated assay. In another embodiment, multiplicate cell motility cell assay devices may be used for comparatively evaluating one or more test compounds for the ability to attract or repel a specified type of motile or chemotactic cell. In this embodiment, the test compound (and suitable controls) are placed in an array of target chambers 22, each connected by a flow channel 20 to a single receiving well 32. Assays are initiated by placing a sample of the selected cell type into the receiving well. Test compounds are evaluated relative to their ability to impede or enhance motility of the selected cell type.

In an alternative embodiment, a selected array of motile or chemotactic cells may be evaluated for their response to a single test compound. In this embodiment, the respective target chambers of the device are utilized as receiving wells for the array of motile cells and the receiving well is utilized as a target chamber (i.e. the typical flow pattern is reversed). In this embodiment, the target chambers are preferably fabricated with flow guiding ribs, while the receiving wells need not be. Samples containing the motile or chemotactic cells to be tested are applied to target chambers 22, and the assay is initiated by placing a sample of the test compound into receiving well 32. The effect of the test compound on the motility of the selected motile or chemotactic cells is then evaluated by then observing movement of those cells through the flow channel from the target chambers 22 to receiving well 32.

Although multiplicate cell motility assay chips having identical channels are illustrated in FIGS. 5–7, it will be appreciated by those skilled in the art that devices having channels of different configurations or lengths may also be constructed, to perform other comparative motile cells assays.

Devices of the invention may be designed for selectively separating, and optionally collecting, a selected population of motile cells on the basis of physical or chemical characteristics of the cells. Such physical or chemical characteristics include, but are not limited to, motility, size, movement in an electrical field, surface morphology (e.g., possession of unique surface antigens), and the like. In a preferred embodiment, devices are designed to selectively separate, and optionally collect, enriched populations of sperm containing male (Y) or female (X) sex chromosomes referred to as "Y" or "X" sperm. It is known that Y sperm tend to swim slightly faster than X sperm due to the slightly reduced weight of the truncated Y chromosome. Accordingly, sperm populations enriched in the Y chromosome may be separable from X chromosome-enriched sperm populations on the basis of motility. Other morphological features that can be used to selectively separate Y from X sperm include differing density, differing motility behavior in an electric field (Y sperm migrate preferentially to the anode) and potentially different and/or unique surface antigens. Accordingly, various separation techniques may be adapted for use in devices of the invention, including, but not limited to: immunoaffinity separation, electrophoresis, gel filtration and density gradient separation.

Figure 8:
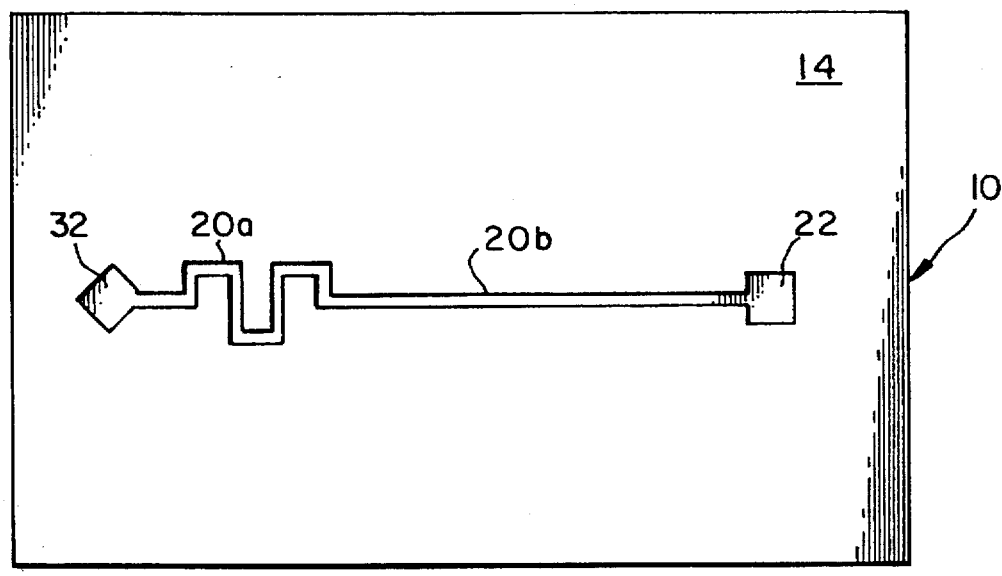
FIG. 8 is view similar to FIG. 5, showing a substrate 14 with a flow channel 20 leading from a receiving well 32 to a target chamber 22. Flow channel 20 is separated into two sections, a first section 20a being a tortuous channel and a second section being selection channel 20b for performing operations on the test sample in its flow from the receiving well 32 to the target chamber 22.
Figure 9A:
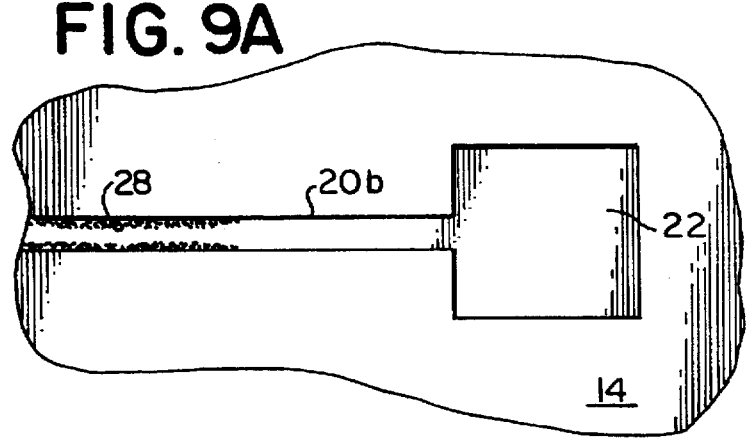
FIG. 9A is an enlarged fragmentary view of substrate 14 similar to FIG. 8, in which the selection section 20b of the flow channel is provided with a coating 28 for selecting a specified component of the sample.
Figure 9B:
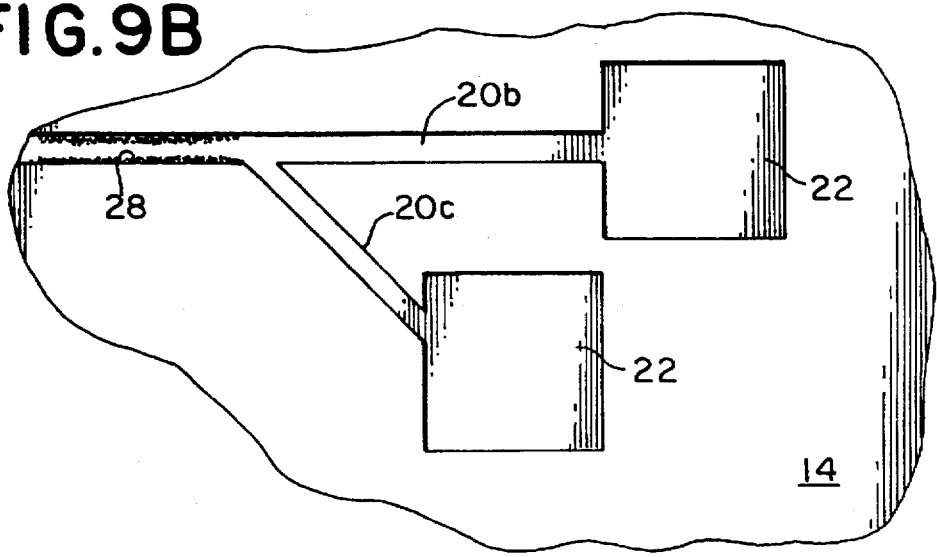
FIG. 9B is a view similar to FIG. 9a, in which the selection section 20b of the flow channel is provided with a branch conduit 20c for diverting selected components of the sample.

Substrates fabricated for various sperm selection devices are shown schematically in FIGS. 8, 9A, and 9B. FIG. 8 shows a substrate 14 that includes receiving well 32 and target chamber 22, connected by a multi-component flow channel comprising a tortuous section 20a and selection section 20b. In this embodiment, the tortuous section 20a typically is fabricated with rounded corners to form a serpentine configuration. The selection section 20b of the flow channel is designed to select a specific cell population (i.e. X versus Y sperm) on the basis of one or more additional chemical or physical features. In one embodiment, an electric field is applied to the selection section of the flow channel, in such a manner that motility of the already faster Y sperm along the flow channel is further enhanced (e.g., by placing the anode proximal to the target chamber) such that the target chamber will include a male chromosome-enriched sperm population. The electric field is applied across the length of the selection section 20b by inserting electrodes into access ports at each end of the selection section; cell movement is then induced by applying the electric field.

In another embodiment illustrated in FIGS. 9A and 9B, the selection section 20b of the flow channel contains a coating in at least a portion thereof, of a capture or restraining agent, such as an antibody directed to a unique surface antigen of one cell population desired to be selected out. For example, the selection section may be coated with an antibody against cell surface antigen specific for X or Y sperm, such that this sperm population is restrained in the selection section, while the unrestrained sperm proceed to target chamber 22. In an alternative embodiment, illustrated in FIG. 9b, the substrate is fabricated with a branch conduit 20c and second target chamber 22 for collecting a second cell population. For example, X or Y sperm restrained by the capture agent of coating 28 subsequently may be released from the capture agent and diverted through branch conduit 20c to the target chamber 22.

Figure 10A:
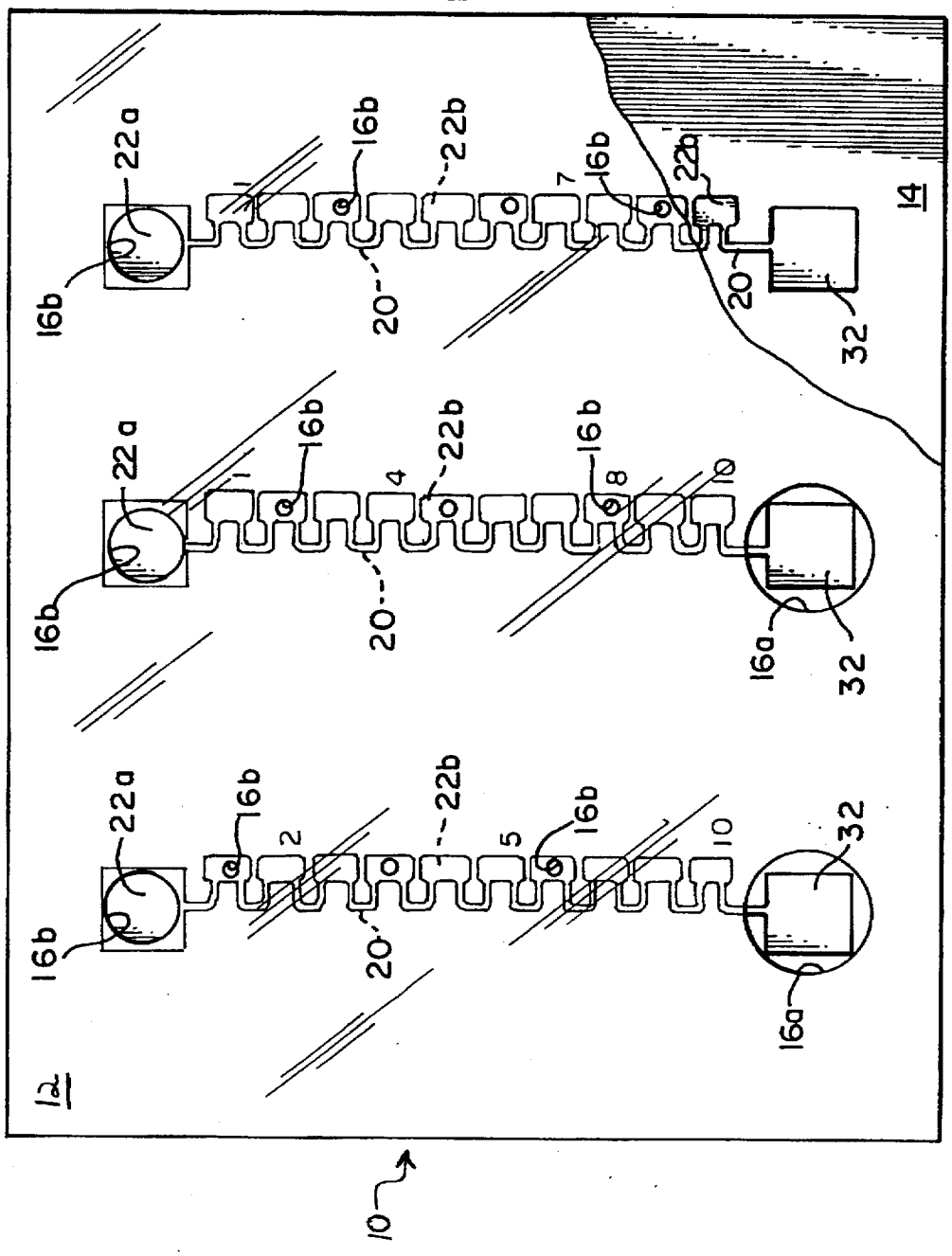
FIGURE 10A is a view similar to FIG. 4, illustrating another embodiment of device 10 in which the substrate 14 is provided with multiple flow channels 20 adapted to include sampling chambers 22b, the cover 12 for said substrate providing access ports 16B to different parts of the flow channels, sampling chambers 22b and target chamber 22a. Numerical markings (some of which are shown) are etched into substrate 14, adjacent to sampling chambers 22b.
Figure 10B:
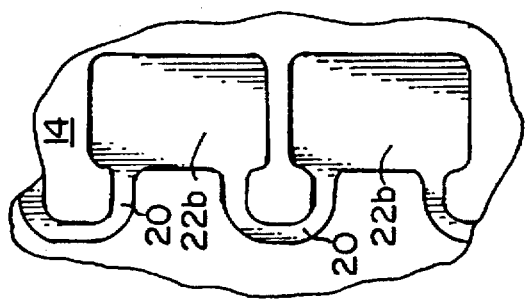
FIG. 10B is an enlarged fragmentary view of substrate 14 shown in to FIG. 10a, showing a flow channel 20 adapted to include sampling chamber 22b.
Figure 13:
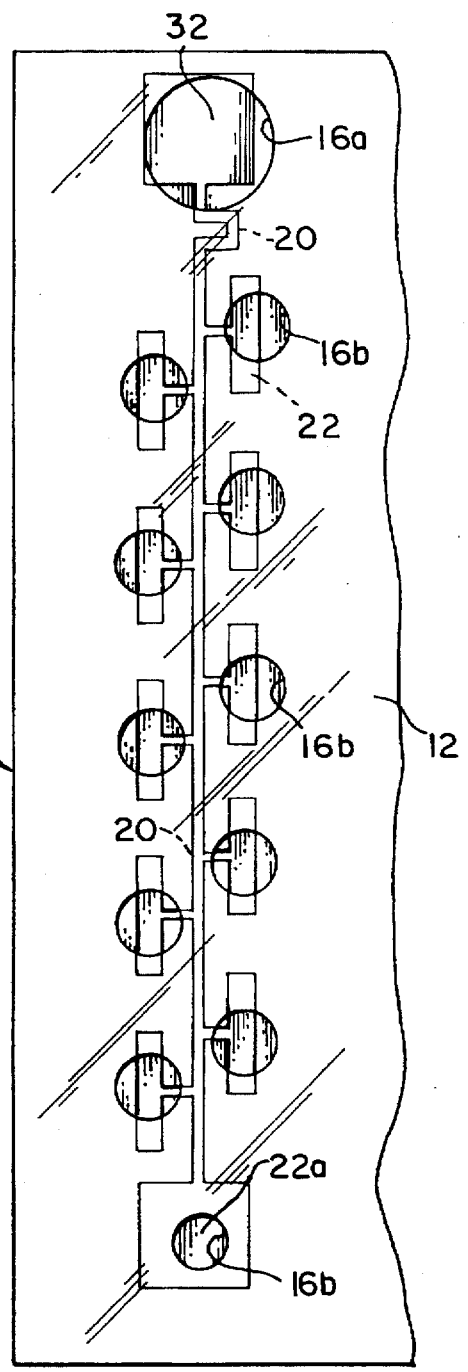
FIG. 13 is a fragmentary face view of another embodiment of device 10 having flow channel 20 and multiple sampling chambers 22b disposed along the length of the flow channel 20.

Another example of a preparative motile cell collecting chip is illustrated schematically in FIG. 10A, 10B, and FIG. 13. FIG. 10A shows a device 10, wherein the substrate 14 is fabricated with a receiving well 32 and a target chamber 22a, connected by a modified tortuous flow channel 20, wherein the channel comprises a series of sampling chambers 22b, formed by expanding the symmetrically serpentine tortuous flow channel 20 along the turns of the channel on one side. In a preferred embodiment, the substrate is etched (or otherwise marked) with lines of demarcation and/or reference numbers (or other designations) at various points along the flow path (e.g., at each sampling chamber in the device shown in FIG. 10A), for facilitating measurements of cell motility. An enlarged view of a section of flow channel 20 comprising sampling chamber 22b (with reference numbers adjacent thereto) is shown schematically FIG. 10B. FIG. 10A illustrates a device having three identical flow systems. The device illustrated in FIG. 10A comprises the above-described substrate 14 covered by a cover 12, fabricated to include inlet ports 16a and access ports 16b disposed over and in registry with the receiving well, target chamber, and sampling chambers, respectively, at selected locations. Access ports 16b disposed over the tortuous flow channels 20 are arranged such that samples may be removed at various points along the flow path between the receiving well and the target chamber. As illustrated in FIG. 10A, which shows a device containing three identical tortuous flow channels and sampling chamber arrays, access ports 16b are offset over the sampling chambers such that each access port provides access to a different sampling chamber within the channels.

An alternative embodiment of a preparative motile cell collecting chip is shown in FIG. 13. FIG. 13 illustrates a device comprising substrate fabricated with a receiving well 32 and target chamber 22a, connected by a flow channel 20 which branches into a series of sampling chambers 22b. The substrate is covered by a cover 12 fabricated to comprise inlet port 16a and various access ports 16b for accessing the target chamber and various sampling chambers. It should be noted that in all of the multiport devices described above, flow properties of the sample fluid may be improved by sealing some or all of the access ports during the assay.

Figure 11:
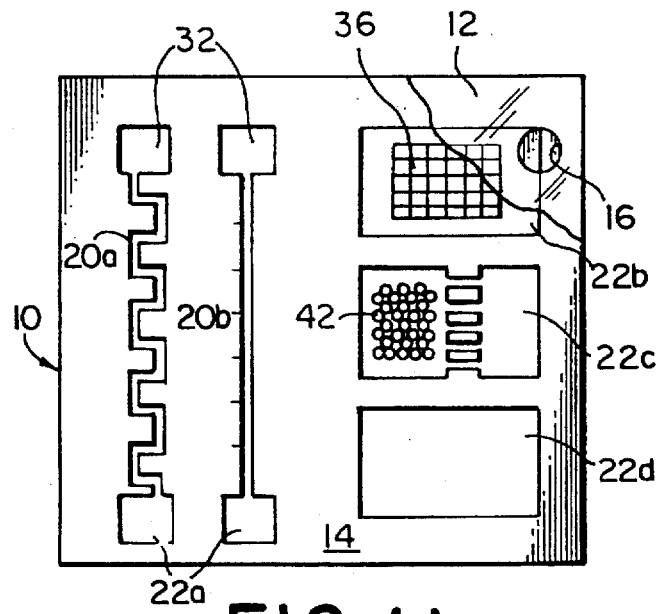
FIG. 11 is face view of a device 10 with the cover 12 broken away to illustrate the substrate 14 with receiving wells 32, flow channels 20 and chambers 22 for performing different evaluations or analyses of a test sample.
Figure 12:
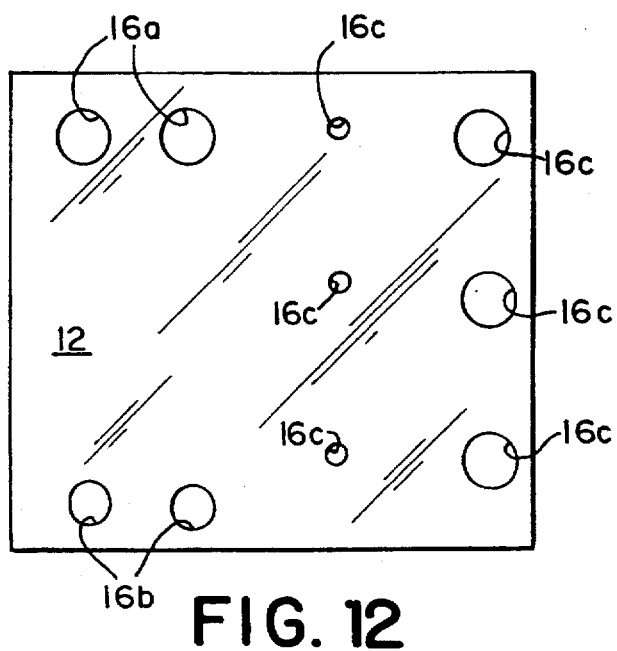
FIG. 12 is face view of the complete cover 12 which is broken away in FIG. 11.

It is often advantageous, particularly with reference to sperm analysis, to conduct two or more different types of assays on a single cell sample, preferably simultaneously. Devices of the invention may be fabricated with various configurations and reagents, for the purpose of conducting a plurality of assays on a single sample. A device for conducting multiple assays on a single sperm sample is illustrated in FIG. 11 and FIG. 12. Device 10 shown in FIG. 11 is fabricated with structures for five different sperm tests. Substrate 14 comprises a receiving well 32 connected by a tortuous flow channel 20a to a target chamber 22a, for sperm motility testing. Substrate 14 further comprises another receiving well 32 connected to a target chamber 22a by a non-tortuous flow channel 20b, pre-filled with a hyaluronic acid solution and having various lines of demarcation adjacent thereto, for conducting a sperm penetration test. Substrate 14 further contains chamber 22b for conducting a sperm count using a conventional grid 36. Substrate 14 further comprises chamber 22c in which is disposed, e.g. antibody coated microparticles, for conducting a sperm antibody test. Substrate 14 further contains chamber 22d, which may be pre-filled with a substance such as Resazurin dye, for conducting a sperm vitality test. Cover 12 of device 10 shown in FIG. 11 is shown in full in FIG. 12. As can be seen in FIG. 12, cover 12 is fabricated with various inlet ports and access ports, in registry with the wells and chambers of substrate 14, for adding samples and reagents to the multiple sperm testing device 10. In practice, a small sample of liquified semen is applied to the different test areas on the chip. After a few minutes, the results of each test is assessed visually, using, e.g. a microscope at, e.g., 600× magnification. Results would be available within a few minutes, thereby permitting an attending physician or clinician to report and/or select an appropriate course of action during the course of an office visit by a patient.

Figure 14:
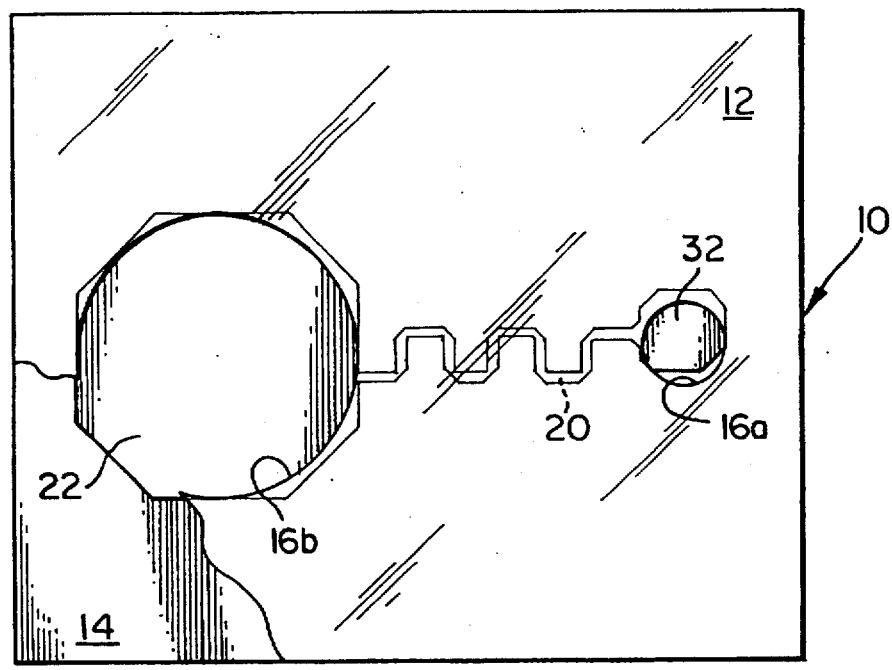
FIG. 14 is face view of device 10, having a configuration of receiving well 32, flow channel 20 and target chamber 22 that is different from the configurations shown in previous embodiments, being adapted for in vitro fertilization of an egg disposed in target chamber 22.
Figure 16:
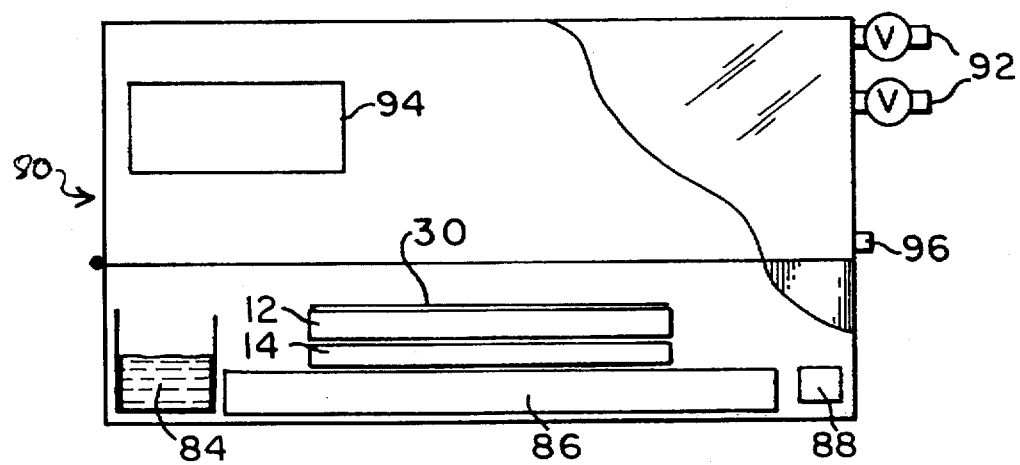
FIG. 16 is partially diagrammatic view of a portable incubator 80 with portions broken away to show the components contained in the incubator.
Figure 15:
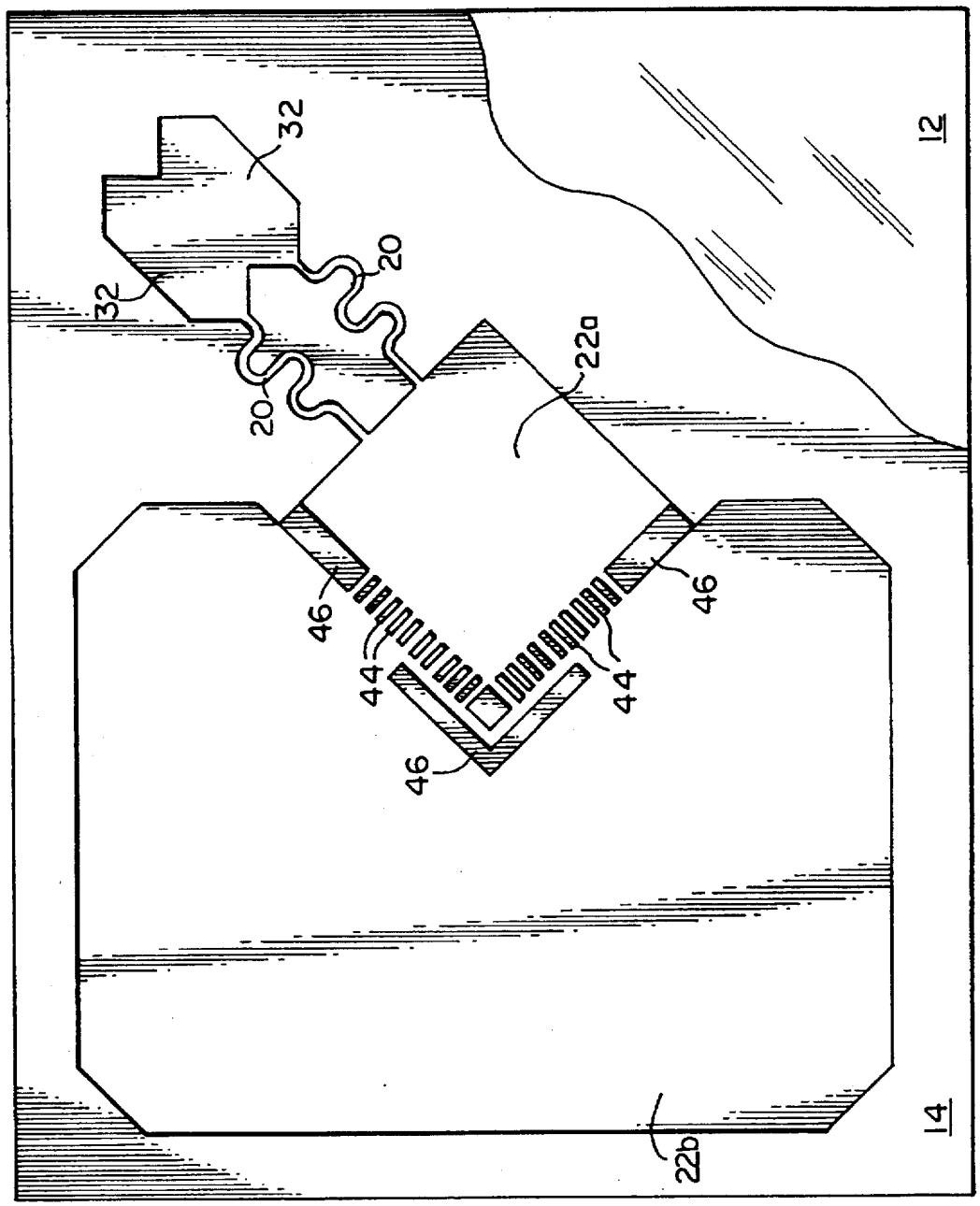
FIG. 15 is a view of an in vitro fertilization device 10, which further comprises a fluid reservoir chamber 22b.

In another embodiment, the devices of the invention may be utilized to perform an in vitro fertilization, which advantageously may be conducted in a small, portable controlled environment chamber (i.e. an incubator). Embodiments of in vitro fertilization devices and a portable incubator are shown in FIGS. 14–16. Device 10 in FIG. 14 includes a substrate 14 into which is fabricated a receiving well 32 and a tortuous flow channel 20, terminating in an enlarged target chamber 22 suitable to contain one or more eggs to be fertilized. The device includes a cover 12, which is disposed over the substrate 14, with ports 16a and 16b positioned over the receiving well and target chamber, respectively. An alternative in vitro fertilization device is shown in FIG. 15. Device 10 in FIG. 15 comprises substrate 14, into which is fabricated a dual receiving well 32, from which extend tortuous flow channels 20, which terminate in a target chamber 22a, of sufficient size to contain one or more eggs to be fertilized. Target chamber 22a is in fluid communication with reservoir chamber 22b, which is designed to contain a reservoir of biologically compatible medium for purposes of maintaining appropriate fluid balances in the in vitro fertilization device. Disposed between reservoir chamber 22b and target chamber 22a are a series of walls 46 and posts 44 designed to restrain eggs nesting in target chamber 22a (and, to a certain extent, sperm that have entered the target chamber), but to permit fluid communication between the target chamber 22a and the reservoir chamber 22b. The receiving wells 32 of both fertilization devices shown in FIG. 14 and 15 are preferably fabricated with cell directors comprising flow-guiding ribs (not shown).

The in vitro fertilization chips shown in FIG. 14 and 15 may be used in conjunction with a small, portable incubator to control ambient conditions for in vitro fertilization. An example of such an incubator is shown in FIG. 16. As shown in FIG. 16, the incubator 80 comprises a substantially airtight chamber having a region for holding the in vitro fertilization chips. The incubator 80 is fitted with sensors or other means 94 to detect ambient microenvironmental conditions within the incubator 80, and further comprises one or more valves 92 for filling the chamber with gas of appropriate composition. Alternatively, the incubator 80 may be constructed with a chemical gas generating component 88, for purposes of altering or maintaining the gas composition within the incubator. The incubator 80 further comprises a heater 86 and a humidifier 84, both in electronic communication with ambient condition sensing device 94. In practice, an appropriately prepared in vitro fertilization chip is placed in the incubator, which has been precharged with fluid and preheated to an appropriate temperature, e.g., 37° C. The incubator chamber is filled with a gas mixture of the appropriate composition (5% oxygen, 5% carbon dioxide, and 90% nitrogen, for example). The chip is incubated for an appropriate period (e.g. 24 hours) after which eggs are inspected for fertilization and development using an optical device, such as a microscope.

Observation of eggs in the target chamber may be accomplished directly through the top of the incubator lid, which is preferably comprised of a transparent material, thereby causing minimal distress to the developing embryo. Alternatively, the lid may be raised by a handle 96 to provide direct access to the device.

The invention will be understood further from the following nonlimiting examples.

EXAMPLE 1

Sperm motility was assessed using a device 10 of a type shown schematically in FIG. 10A.

Specifically, substrate 14 of the device included receiving wells 32 and target chambers 22a, which consisted of 40 µm-deep square troughs (2×2 mm and 1×1 mm, respectively), connected by sample flow channels 20 (100 µm wide×40 µm deep), adapted to comprise sampling chambers 22b. The substrate was covered with a Pyrex glass cover, having holes drilled through it, positioned above and registered with the receiving wells 32 and target chambers 22 (holes in the glass cover in registry with various sampling chambers were optionally included in some devices). The substrate was comprised of a silicon wafer 400 µm in thickness. Masks for the fabrication process were made by Align-Rite (Santa Clara, Calif.). The silicon wafers used for the substrate (approximately 10 cm in diameter) were etched by Micrel Semiconductor (San Jose, Calif.) and diced into 17×14 mm chips by the Alberta Microelectronics Centre (Edmonton, Alberta, Canada) Pyrex glass tops with appropriate holes drilled therein (obtained from Mooney Precision Glass, Huntington W.V.) were bonded to the substrate by use of a diffusive bonding process (G. Wallis, *J. Am. Ceram. Soc.*, 53: 563–567, 1970). The circular chambers formed by the holes through the glass above the receiving wells were 4.22 µl in volume, and the holes disposed above the target chambers were of a volume of 1.55 µl.

The channels and chambers of the device were pre-filled with HEPES-buffered human tubal (HTF) medium (Irvine Scientific, Santa Ana, Calif.) containing 5 g/l bovine serum albumin (Cohn Fraction V, Sigma Chemical Co., St. Louis, Mo.) (HTF/BSA). Next, a 2- µl sample of liquified semen was introduced into the receiving wells 32 by pipette. The progression of sperm into the channels was then monitored with a microscope (Aristomet, Wild Leitz, Heerbrugg, Switzerland) and recorded with a black-and-white television camera (Dage-MTI, Michigan City, Ind.) and a video cassette recorder (PVM-122, Sony, Teaneck, N.J.). A numerical scale (10 to 1 in the direction from the receiving well to the target chamber) was etched into the silicon next to the channels to facilitate semiquantitative assessment of the progression of sperm along the channels. Sperm progression was observed at five minute intervals from 0–25 minutes.

Sperm were detected in the entrance to the flow channel (scale position 10) within a few minutes; by 25 minutes, a large population of motile sperm were distributed along half the length of the channel (scale points 10 to 6). The sperm may optionally be removed from various points along the flow channels and chambers through access ports 16a and 16b, disposed over the target chambers 22a and various sampling chambers 22b.

EXAMPLE 2

Figure 4:
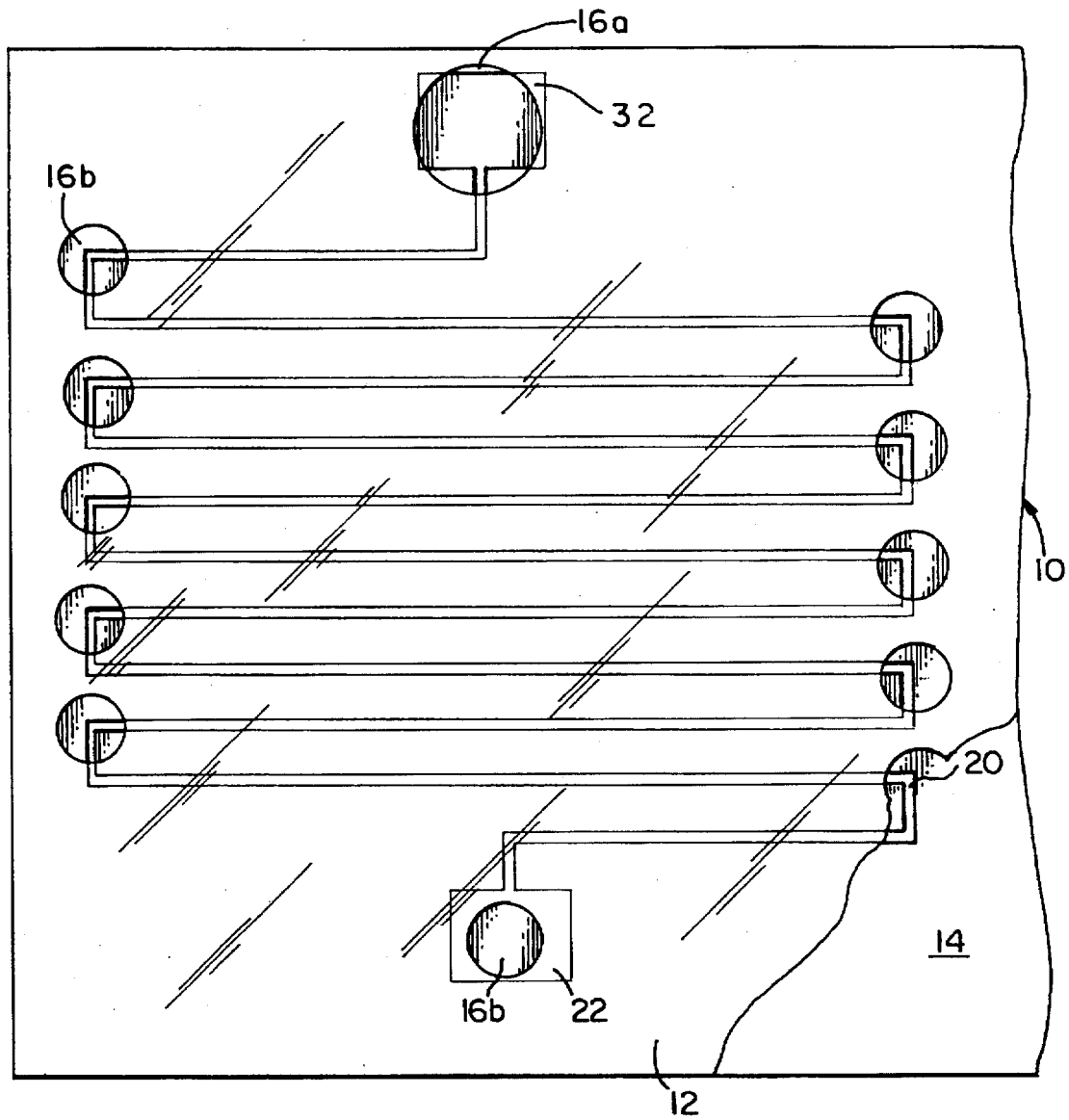
FIG. 4 is a fragmentary face view of device 10 in which the substrate 14 is provided with a tortuous flow channel 20 extending from a receiving well 32 to a target chamber 22, a portion of the cover 12 being broken away for the purposes of illustration.

In another procedure, a device 10 of a type shown schematically in FIG. 4 was used to test a series of three semen samples previously analyzed and graded as having normal, borderline, and abnormal mobility, respectively. Assay procedures for this example were the same as those described for Example 1 above.

The comparative migration distances of the sperm along the channel 20 reflected the previous gradation of the sperm samples as normal, borderline, abnormal. The normal sperm sample migrated farthest along the channel, while the borderline sperm sample migrated less far and the abnormal sperm sample migrated the least distance.

EXAMPLE 3

Sperm motility was assessed and compared using a tortuous-channeled device 10 of a type shown schematically in FIG. 4 and a straight-channeled device similar to the straight channel portion of the multiple assay device 10 shown in FIG. 11. As described above, the flow channels were pre-filled with HTF/BSA medium and samples of liquified semen (2 µl) were applied to receiving wells 32. The sperm were then allowed to swim into the channels 20 for 10 minutes, then the number of sperm at specific locations in each channel was determined. For the straight channel design, sperm were monitored at a position 840 µm linearly distant (no right-angled turns) from the receiving well. For the tortuous channel design, sperm were monitored 3100 µm from the receiving well, i.e., after they had negotiated two right-angled turns. As expected, the number of sperm swimming via the tortuous pathways to the more distant observation point was fewer than via the short linear channel.

EXAMPLE 4

An in vitro fertilization is performed using an in vitro fertilization chip of the type illustrated in FIG. 15, in an incubator of the type illustrated in FIG. 16. The in vitro fertilization chip 10 is filled HTF BSA and an egg or eggs are placed in the enlarged target chamber 22a. A small sample of washed semen (e.g., 1 μl) is added to the receiving well 32. The chip is then place in the microincubator 80, which has been precharged with fluids and preheated to 37° C. The incubator chamber is filled a gas mixture comprising 5% oxygen, 5% carbon dioxide, 90% nitrogen. The chip 10 is incubated for approximately 24 hours, and the eggs thereafter inspected for fertilization and development. Inspection of the eggs is accomplished by visualizing target chamber 22a directly through the top of the incubator lid, which is comprised of transparent material, thus causing minimum distress to the developing embryo.

In another procedure, carbon dioxide is generated in the incubator chemically, by mixing hydrochloric acid and a biologically compatible carbonate or bicarbonate salt (e.g. sodium bicarbonate), thereby producing carbon dioxide gas within the incubator.

While certain preferred embodiments of the present invention have been described, illustrated and specifically exemplified above, it is not intended be limited to such embodiments, various modifications may be made thereto without departing from the scope and spirit of the present invention, as set forth in the following claims.

What is claimed is:

1. A method of analyzing a fluid sample having cells characterized by their motility, comprising:
   a) providing a device comprising:
      a solid substrate having a flow system which comprises at least one elongate flow channel of mesoscale cross-sectional dimension, and a receiving well communicating with said at least one channel and defining a starting point in said channel; and
      a cover for said substrate closing said channel and having a first port in registry with said receiving well, for introducing said sample into said receiving well so as to enable the motile cells of the sample to travel from the receiving well to progress points along the at least one channel, said cover further defining a second port in registry with said at least one channel at a point therealong, said flow system being filled with a carrier fluid;
   b) introducing said sample into said receiving well;
   c) controlling the resident conditions of the combined carrier fluid and sample to assure motility of said cells in said carrier fluid;
   d) observing the cells in the flow system;
   e) collecting data based on said observation; and
   f) completing the analysis using said data.

2. A method according to claim 1, wherein said resident conditions are controlled by sealing said second port of said device prior to introducing said sample into said receiving well.

3. A method according to claim 1, wherein said resident conditions are controlled by providing in said receiving well a plurality of flow-regulating solids, said flow-regulating solids having a size and shape effective to permit passage of said motile cells, in non-aggregated form, from said receiving well into said at least one channel and concomitantly to substantially restrain passage into said at least one channel of selected particulate matter in said sample.

4. A method according to claim 11, wherein said resident conditions are controlled by providing in said receiving well a cell director comprising flow-guiding ribs longitudinally aligned with said channel, for directing said motile cells from said receiving well into said at least one channel.

5. A method according to claim 1, which further includes generating replicate sets of said data, by a method comprising:
   a) providing said device, which further comprises a plurality of identical flow systems; and
   b) performing the method of claim 1 simultaneously in each of said plurality of flow systems, thereby generating said replicate sets of data.

6. A method according to claim 1, which further includes conducting a plurality of analyses on a single sample, said method comprising:
   a) providing the device of claim 1, which further comprises a multiplicity of non-identical flow systems designed for said plurality of analyses, each said flow system being filled with a carrier fluid optionally containing reagents for each said analysis;
   b) introducing an aliquot of said single sample into said receiving well of each said flow system;
   c) controlling the resident conditions of each said combined carrier fluid and sample to assure motility of said cells in said carrier fluid;
   d) observing the cells in each said flow system;
   e) collecting data based on said observations; and
   f) completing the plurality of analyses using said data.

7. A method according to claim 1, which further includes selectively collecting at least one motile cell from a sample comprising a mixed population of cell types, said method comprising:
   a) providing the device of claim 1, wherein said at least one channel comprises a selection region, said selection region being adapted for selective separation of said at least one motile cell type from said mixed population of cell types;
   b) introducing said sample into said receiving well, whereafter said mixed population of cell types migrates through said selection region of said at least one channel, resulting in said selective separation of said at least one motile cell type from said mixed population of cell types; and
   c) collecting said at least one motile cell type.

8. A method according to claim 7, wherein said selection region comprises a capture agent which selectively binds said at least one motile cell type.

9. A method according to claim 7, wherein said selection region comprises an electric field which selectively influences motility of said at least one motile cell type.

10. A method according to claim 7, adapted for selectively separating male chromosome-containing sperm from female chromosome-containing sperm, wherein said sample is a sperm sample and migration of sperm therein through said selection region results in substantial separation of a population of said male chromosome-containing sperm from a population of said female chromosome-containing sperm, at least one of said populations being collected.

11. A method of performing an in vitro fertilization, comprising:

a) providing a device comprising:
- a solid substrate having at least one elongate flow channel of mesoscale cross-sectional dimension;
- a receiving well communicating with said at least one channel and defining a starting point in said at least one channel;
- an egg nesting well communicating with said at least one channel and defining a terminating point in said at least one channel; and
- a cover for said substrate closing said at least one channel and having a first port for introducing a sperm sample into said receiving well to enable said sperm to travel from said receiving well through said at least one channel to said egg nesting well, said cover further comprising a second port in registry with said egg nesting well, said device containing in vitro fertilization medium;

b) introducing at least one egg into said egg nesting well;

c) introducing a sperm sample into said receiving well; and d) placing said device into a portable, sealable, environmental control chamber for a time and under conditions effective to enable said sperm to travel to said egg and to fertilize said egg.

12. A method according to claim 11 wherein said device is placed in said environmental control chamber that further comprises at least one of

- an atmosphere producing system for producing an atmosphere in said chamber conducive for said in vitro fertilization;
- a temperature regulator for controlling temperature within said chamber; and
- a humidity controller for controlling humidity within said chamber.

13. A device for analyzing a sample having cells characterized by their motility, the device comprising:

- a solid substrate having a flow system which comprises at least one elongate flow channel of mesoscale cross-sectional dimension, and a receiving well communicating with said at least one channel and defining a starting point in said at least one channel, said at least one channel comprising a selection region, said selection region being adapted for selective separation of at least one motile cell type from a mixed population of cell types and comprising an electric field which selectively influences motility of said at least one motile cell type; and

- a cover for said substrate closing said at least one channel and having a first port in registry with said receiving well, for introducing a sample containing motile cells into said receiving well so as to enable the motile cells of the sample to travel from the receiving well to progress points along the channel, said cover defining a second port to said at least one channel at a point therealong.

* * * * *

UNITED STATES PATENT AND TRADEMARK OFFICE
CERTIFICATE OF CORRECTION

PATENT NO. : 5,744,366
DATED : April 28, 1998
INVENTOR(S) : Larry J. Kricka and Peter Wilding It is certified that error appears in the above-identified patent and that said Letters Patent is hereby corrected as shown below:

Column 20, line 6, change "11" to -- 1 --.

Signed and Sealed this

Twenty-eighth Day of July, 1998

*Attest:*

*Attesting Officer*

BRUCE LEHMAN
*Commissioner of Patents and Trademarks*